US011129979B2

(12) United States Patent
Gibson

(10) Patent No.: US 11,129,979 B2
(45) Date of Patent: Sep. 28, 2021

(54) METHODS AND DEVICES FOR LOCALIZING COMPOSITIONS

(71) Applicant: REGRESAR MEDICAL, INC., San Diego, CA (US)

(72) Inventor: Hal William Gibson, Long Beach, CA (US)

(73) Assignee: Regresar Medical, Inc., San Diego, CA (US)

( * ) Notice: Subject to any disclaimer, the term of this patent is extended or adjusted under 35 U.S.C. 154(b) by 0 days.

(21) Appl. No.: 16/890,580

(22) Filed: Jun. 2, 2020

(65) Prior Publication Data

US 2020/0289807 A1    Sep. 17, 2020

Related U.S. Application Data

(63) Continuation of application No. PCT/US2020/018979, filed on Feb. 20, 2020.

(60) Provisional application No. 62/807,929, filed on Feb. 20, 2019, provisional application No. 62/812,228, filed on Feb. 28, 2019, provisional application No. 62/878,030, filed on Jul. 24, 2019.

(51) Int. Cl.
| | |
|---|---|
| *A61N 1/04* | (2006.01) |
| *A61N 2/00* | (2006.01) |
| *A61M 35/00* | (2006.01) |
| *G01N 33/50* | (2006.01) |
| *A61K 31/185* | (2006.01) |
| *A61K 31/00* | (2006.01) |

(52) U.S. Cl.
CPC .......... *A61N 1/0456* (2013.01); *A61M 35/00* (2013.01); *A61N 1/0452* (2013.01); *A61N 2/002* (2013.01); *A61K 31/00* (2013.01); *A61K 31/185* (2013.01); *G01N 33/50* (2013.01)

(58) Field of Classification Search
CPC .... G01N 33/50; G01N 33/483; A61K 31/185; A61K 31/00; A61K 9/7007; A61N 2/002; A61N 5/00; A61N 1/0456; A61N 1/0452; A61M 35/00
See application file for complete search history.

(56) References Cited

U.S. PATENT DOCUMENTS

2018/0141982 A1* 5/2018 Anderson .......... A61K 38/4893

FOREIGN PATENT DOCUMENTS

WO    WO-2017172838 A1 * 10/2017 ............... A61M 5/46

OTHER PUBLICATIONS

STIC SEASRCH (Year: 2020).*

* cited by examiner

*Primary Examiner* — Lauren P Farrar
*Assistant Examiner* — Hamza A Darb
(74) *Attorney, Agent, or Firm* — Wagenknecht IP Law Group PC

(57) ABSTRACT

Methods for limiting dissipation of neurotoxins and dermal fillers from an injection site are disclosed, which includes applying a repellant electric field to the skin around the injection site to limit dissipation of an injected neurotoxin or dermal filler.

28 Claims, 2 Drawing Sheets

METHODS AND DEVICES FOR LOCALIZING COMPOSITIONS

CROSS REFERENCE TO RELATED APPLICATIONS

This application is a continuation of PCT/US2020/018979, filed Feb. 20, 2020, which claims priority to U.S. provisional patent application No. 62/807,929 filed Feb. 20, 2019, U.S. provisional patent application No. 62/812,228, filed Feb. 28, 2019, and U.S. provisional patent application No. 62/878,030, filed Jul. 24, 2019, each of which is incorporated by reference herein in its entirety.

TECHNICAL FIELD

The invention relates to systems, methods, and devices for localizing materials administered to mammals, for example through injection.

BACKGROUND

Injections are a common method of introducing materials, for example therapeutic materials, into patients. However, such injections carry the risk of unwanted dispersion or dissipation of the materials beyond a desired treatment site. For example, adverse effects can result when neurotoxin injections spread beyond a treatment site; in the case of glabellar line or "crows feet" injections, eye droop or "ptosis" can occur. Neck weakness or difficulty swallowing can occur as a result of injections to the head. Further, immune response can be increased when injected materials spread from desired treatment sites. In the case of dermal filler injections, the injected material can spread beyond the treatment site, causing unwanted cosmetic effects, for example when treating the lip or cheekbones.

It is known that electrical stimulus can affect the movement of molecules, biologics, etc., and that electromagnetic forces including electric currents, charges, fields, magnetic fields, etc., can be used therapeutically. For example, iontophoresis is a process of transdermal drug delivery by use of a voltage gradient on the skin. Molecules (for example, drugs or biologics) are transported across the stratum corneum by electrophoresis (the motion of dispersed particles relative to a fluid under the influence of a spatially uniform electric field) and electro-osmosis (the motion of liquid induced by an applied potential across a porous material). During iontophoresis, a small electric current is applied to an iontophoretic chamber placed on the skin, containing a charged active agent and its solvent vehicle. Another chamber or a skin electrode carries the return current. One or two chambers are filled with a solution containing an active ingredient and its solvent vehicle. The positively charged chamber, called the anode, will repel a positively charged chemical species, whereas the negatively charged chamber, called the cathode, will repel a negatively charged species into the skin.

It is known that low-voltage iontophoresis equipment can safely "drive" molecules over 1 cm into the tissue beneath the skin, using safe, well-tolerated voltages and currents. Such depths are suitable for methods disclosed herein, as many injected materials are administered just below the skin or at a minimum depth intramuscularly. Therefore, these safe, well-tolerated voltages and currents used in iontophoresis can also be used to control material dissipation by, rather than using a repellant force to drive a material into the skin, using that repellant force to "fence" or limit the material to a desired treatment area. In addition to the repellant force, an attractive force can also be used to localize an administered material.

SUMMARY

Iontophoresis provides an alternative to injection. However, iontophoresis does not offer the precision of other administration modes, for example a needle. Therefore, an object of the instant Specification is to provide improved administration methods that utilize traditional administration methods such as injection combined with electromagnetic forces such as electric charges, fields, and currents to control post-administration dissipation. In embodiments, an electric charge can be used to attract or repel an administered material—an "attractive" force can be used to increase localization of an injected material, for example by applying an attractive force to a treatment area, while a "repellant" force can be used to decrease dissipation of an administered material, for example by "fencing" the treatment area or aspects thereof with the repellant force.

Embodiments comprise methods, systems, and devices for localizing or minimizing the spread or dissipation of injected materials, for example injected pharmaceutical compositions. Embodiments comprise the use of, for example, an energy field, for example an electromagnetic field (EMF) such as an electric field, an electric charge, an electric current, a magnetic field, or combinations thereof, to localize injected compositions. Injected compositions can comprise, for example, biologics, neurotoxins, proteins, DNA, viruses, dermal fillers, and the like.

Embodiments comprise methods, systems, and devices for increasing the spread or dissipation of injected materials, for example injected pharmaceutical compositions. Embodiments comprise the use of, for example, an energy field, for example an electromagnetic field (EMF) such as an electric field, an electric charge, an electric current, a magnetic field, or combinations thereof, to dissipate injected compositions. Injected compositions can comprise, for example, biologics, neurotoxins, proteins, DNA, viruses, dermal fillers, and the like.

Embodiments comprise methods, systems, and devices for directing the spread or dissipation of injected materials, for example injected pharmaceutical compositions. Embodiments comprise the use of, for example, an energy field, for example an electromagnetic field (EMF) such as an electric field, an electric charge, an electric current, a magnetic field, or combinations thereof, to localize injected compositions. Injected compositions can comprise, for example, biologics, neurotoxins, proteins, DNA, viruses, dermal fillers, and the like.

Localizing the injected materials can eliminate or reduce the spread or dissipation of the materials, thereby eliminating or reducing the risk of unwanted effects, as well as minimizing the "immunogen footprint" that can result from an injection. Localizing the materials can increase the effect duration of injected materials, for example the effect duration of a neurotoxin injection, or the effect duration of a dermal filler injection. Localizing the materials can increase the effect intensity of injected materials, for example the effect intensity of a neurotoxin injection, or the effect intensity of a dermal filler injection.

In embodiments, a material is injected subcutaneously to, for example, between 1 and 15 mm depth, then an attractive force comprising an electric charge is applied to the injection site. The order of this operation can be reversed, such that the force is applied before or after the administration.

In embodiments, a material is injected subcutaneously to, for example, between 1 and 15 mm depth, then a repellant force comprising an electric charge is applied around or partially around the treatment site. The order of this operation can be reversed, such that the force is applied before or after the administration.

In embodiments, a material is injected subcutaneously to, for example, between 1 and 15 mm depth, then an attractive force comprising an electric charge is applied to the injection site, and a repellant force comprising an electric charge is applied around or partially around the treatment site, wherein the attractive and repellant forces comprise opposite electric charges. The order of this operation can be reversed, such that the force is applied before or after the administration. In embodiments, the attractive and repellant forces establish an electric field. In embodiments wherein there is electrical conductivity between the attractive and repellant forces, an electric current can be established.

Embodiments can comprise neurotoxin administrations to treat, for example, pain, muscle-related conditions, depression, cosmetic concerns, and combinations thereof. For example, to treat pain, muscle-related conditions, depression, cosmetic concerns, and the like, an attractant force, for example the attractant electrode (determined based upon the physical properties of an injected material) of a TENS device can be placed on top of or in the vicinity of the injection site of a neurotoxin, with the repellant electrode of the device placed, for example, an inch or less from the attractant electrode. Clinically, TENS is applied at varying frequencies, intensities, and pulse durations of stimulation. By means of electrodes, electric flow from TENS unit is converted into an ionic current flow in the living tissue. During TENS therapy, pulsed electrical current is generated either by A.C. mains or using batteries (usually 9V) and delivered across the intact skin surface via electrodes. In the case of methods utilizing TENS, the attractant electrode can be placed over the injected material treatment site.

Disclosed embodiments comprise "active" devices that utilize a power source such as AC or DC power or pulsed RF or pulsed current, such as high voltage pulsed current, or "passive" devices that do not require external power. For example, in passive embodiments, the electrical energy can be derived from dissimilar metals creating a battery, for example wherein the dissimilar metals are located on a separate dressing or bandage, whereas those embodiments with an external power source can require conductive electrodes in a spaced apart configuration to predetermine the electric field shape and strength. In active devices, AC or DC current can be used. For example, an exemplary active device suitable for use with disclosed embodiments comprises a TENS device.

Aspects disclosed herein comprise bioelectric devices that comprise electrodes. Such matrices can include an electrode formed from a first conductive material, the material including a metal species; and a second electrode formed from a second conductive material, the material including a metal species capable of defining at least one voltaic cell for spontaneously generating at least one electrical current with the metal species of the first electrode when said first and second electrodes are connected via an electrolytic solution such as that within the body, and said first and second electrodes are not in physical contact with each other. Certain aspects utilize an external power source such as AC or DC power or pulsed RF or pulsed current, such as high voltage pulsed current.

Further disclosed embodiments can comprise articles of manufacture that include packaging material and an amount of a chemo-denervating agent, for example a neurotoxin. The chemo-denervating agent can be a Clostridial neurotoxin, for example a botulinum toxin such as botulinum toxin A (BoNT/A), botulinum toxin B (BoNT/B), botulinum toxin E (BoNT/E), botulinum toxin F (BoNT/F), combinations thereof, and devices as disclosed herein. These articles of manufacture can comprise kits, for example comprising a neurotoxin or combinations thereof, disclosed devices, and instructions for use.

Disclosed embodiments comprise articles of manufacture that includes packaging material and an amount of a cosmetic agent, for example a dermal filler such as hyaluronic acid (HA), and devices as disclosed herein. These articles of manufacture can comprise kits, for example comprising a dermal filler or fillers, disclosed systems and devices, and instructions for use.

Further embodiments can comprise a topical agent, for example a cream comprising an attractive EMF, to apply to a treatment area following a treatment. For example, a cream that produces an attractive field can be applied over an injected material treatment site, such as the lips or the glabellar line area.

DETAILED DESCRIPTION

Figure 1:
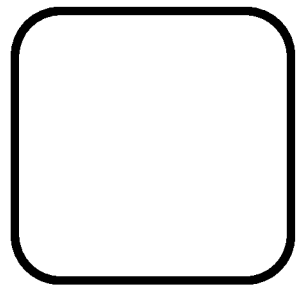
FIG. 1 is an exemplary apparatus 10 configured to produce a repellant electric field and an attractive electric field.
Figure 2:
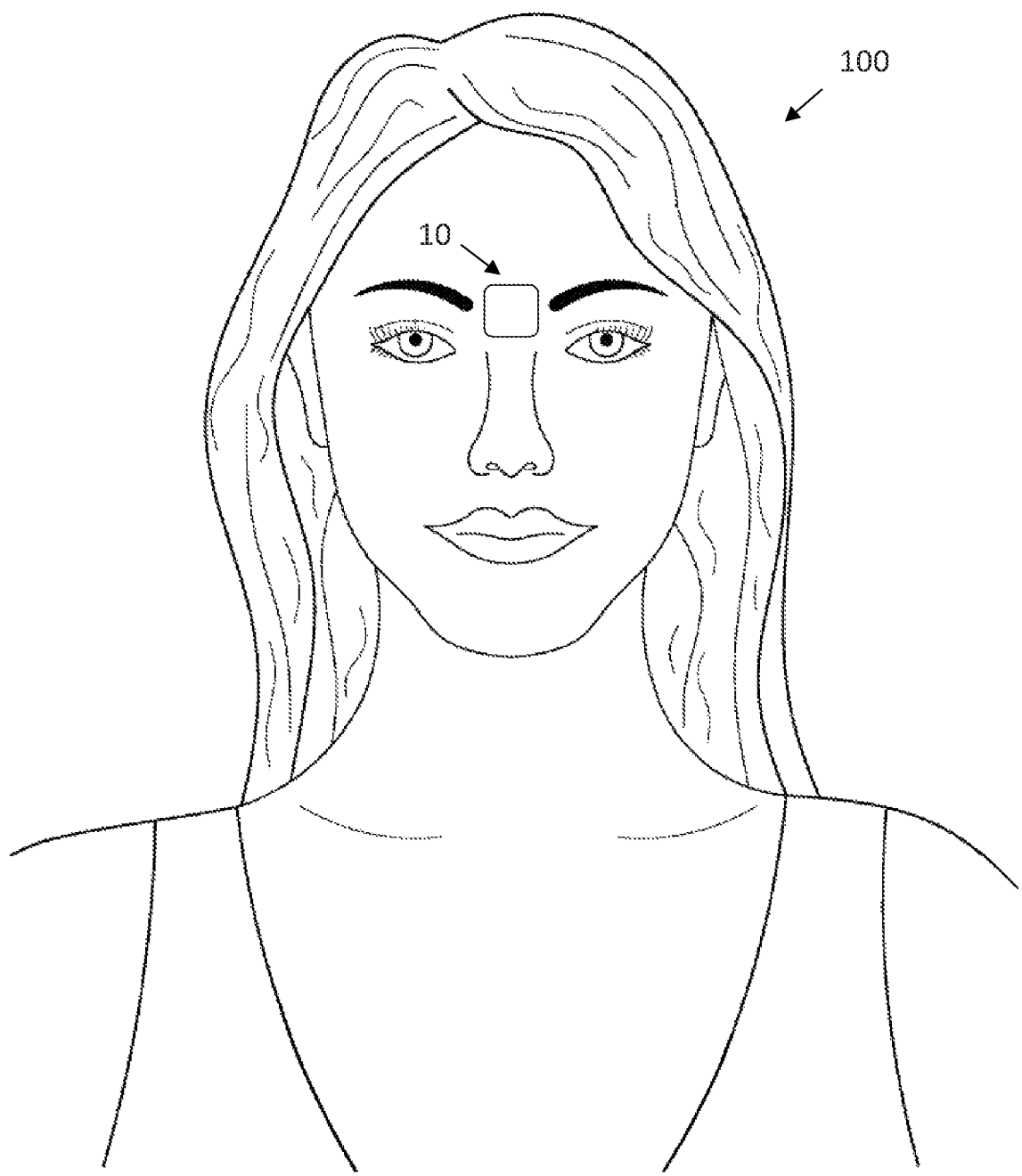
FIG. 2 depicts the apparatus 10 applied against the skin.

The instant disclosure relates to methods for localizing injected materials through use of energy applied to or about the injection site. Such energy can include, for example, electromagnetic energy such as electric energy, electric charge, electric fields, magnetic energy, electric currents, combinations thereof, or the like.

For example, BoNT/A has an isoelectric point of roughly 9.2. Thus, at physiological pH values, BoNT/A carries a net positive charge. In embodiments, by applying a negative source charge to a location, for example a desired treatment or injection location, the toxin can be "fixed" in or attracted to that location. Similarly, by applying a positive source charge to a location, for example around part or all of the perimeter of a treatment site, the toxin can be excluded from that location. Type E (BoNT/E) has an isoelectric point of about 6; therefore, at physiological pH values the toxin carries a net negative charge. This electromotive effect of an electric field on the toxin can be seen in SDS/PAGE images.

Botulinum neurotoxins suitable for use with disclosed methods and systems include, for BoNT/A, BoNT/B, BoNT/C, BoNT/D, BoNT/E, BoNT/F, BoNT/G, BoNT/H, and combinations thereof. Further suitable neurotoxins can comprise the "light chain" of a botulinum toxin. Embodiments can comprise a combination of neurotoxins, for example BoNT/A and BoNT/E. Embodiments can comprise the dissociation of the heavy chain and the light chain, either prior to or following administration. Disclosed embodiments can comprise use of an electric charge, field, or current to dissociate a neurotoxin from accessory proteins or formulation components, for example HSA, either prior to or following an administration, for example an injection.

Embodiments comprise aligning the dipole of a botulinum toxin to provide the correct orientation for binding.

Similarly, dermal fillers can be localized via the disclosed methods. For example, in embodiments, at physiological pH values, hyaluronic acid carries a net negative charge. In embodiments, by applying a positive source charge to a location, the dermal filler can be "fixed" in that location. Similarly, by applying a negative source charge, for example around part or all of the perimeter of a treatment site, the dermal filler can be excluded or repelled from a location.

As seen from electrophoresis gels, the dermal filler's movement can be controlled through use of an electric field, current, or combination thereof. Dermal fillers suitable for use with disclosed methods and systems include, for example, those containing Hyaluronic Acid (HA), Calcium Hydroxylapatite (CaHA), Poly-L-lactic Acid, Polymethylmethacrylate (PMMA), Autologous fat injections (facial fat grafting), and combinations thereof.

Embodiments can also comprise adjusting the pH of an injected material to, for example, the material's isoelectric point, then applying an electric field "perimeter" to localize the material through use of a repellant field.

In embodiments, the electric field can be supplied by a substrate, for example a flexible substrate comprising an electrode of an appropriate charge; for example a positive electrode can comprise silver. A negative electrode can comprise zinc. Embodiments comprise self-contained localization devices that do not require a power supply.

Embodiments comprise devices that require a power supply, for example a power supply connected to electrodes such that one or more electrodes produces a negative electric field, and one or more electrodes produces a positive electric field. Substrates suitable for use with disclosed embodiments can comprise resorbable materials. Substrates suitable for use with disclosed embodiments can comprise clear or opaque materials.

Disclosed embodiments comprise the use of magnetic field to localize injected materials based upon the materials' electrical or magnetic properties. For example, a magnetic field can be used to affect and manipulate the dipole of a molecule, for example a neurotoxin molecule such as BoNT/A, to orient the molecule in a position that increases or decreases the molecule's binding efficiency.

Embodiments comprise modified neurotoxins, said modification comprising increasing the inherent "charge" of the molecule or conductivity of the formulation to increase the effect of disclosed embodiments.

Definitions

"Administration," or "to administer" means the step of giving (i.e. administering) an injected material such as a pharmaceutical composition or active ingredient or dermal filler to a subject. The materials disclosed herein can be administered via a number of appropriate routes, however as described in the disclosed methods, in embodiments the compositions are locally administered by e.g. intramuscular, intradermal, or subcutaneous routes of administration, such as by injection or use of an implant.

"Attractive electromagnetic field" means a charge, field, or current that attracts the injected material, for example an electric field and/or charge.

"Botulinum toxin" or "botulinum neurotoxin" means a wild type neurotoxin derived from *Clostridium botulinum*, as well as modified, recombinant, hybrid and chimeric botulinum toxins. A recombinant botulinum toxin can have the light chain and/or the heavy chain thereof made recombinantly by a non-Clostridial species. "Botulinum toxin," as used herein, encompasses the botulinum toxin serotypes A, B, C, D, E, F, G and H. "Botulinum toxin," as used herein, also encompasses both a botulinum toxin complex (i.e. the 300, 600 and 900 kDa complexes) as well as pure botulinum toxin (i.e. the about 150 kDa neurotoxic molecule), all of which are useful in the practice of the present invention.

"Purified botulinum toxin" means a pure botulinum toxin or a botulinum toxin complex that is isolated, or substantially isolated, from other proteins and impurities which can accompany the botulinum toxin as it is obtained from a culture or fermentation process. Thus, a purified botulinum toxin can have at least 95%, and more preferably at least 99% of the non-botulinum toxin proteins and impurities removed.

"Clostridial neurotoxin" means a neurotoxin produced from, or native to, a Clostridial bacterium, such as *Clostridium botulinum, Clostridium butyricum* or *Clostridium beratti*, as well as a Clostridial neurotoxin made recombinantly by a non-Clostridial species.

"Dermal filler" means compositions used for aesthetic treatments that are injected into or below the skin. Typically, they are designed to effectively reduce the appearance of unwanted wrinkles, contour and create volume, and to revitalize the skin. Suitable fillers can include hyaluronic acid, polyalkylimide, polylactic acid, Polymethyl-methacrylate microspheres (PMMA), and the like.

"Limiting" the dissipation of an administered material means that the total area affected by the administered material is less than the total area would be in the absence of the limiting action.

"Intermediate-acting" as used herein refers to a botulinum toxin that produces effects more slowly that a fast-acting toxin.

"Neurotoxin" means a biologically active molecule with a specific affinity for a neuronal cell surface receptor. Neurotoxin includes Clostridial toxins both as pure toxin and as complexed with one or more non-toxin, toxin-associated proteins.

"Patient" means a human or non-human subject receiving medical or veterinary care.

"Pharmaceutical composition" means a formulation in which an active ingredient can be a neurotoxin, a dermal filler, or the like. The word "formulation" means that there is at least one additional ingredient (such as, for example and not limited to, an albumin [such as a human serum albumin or a recombinant human albumin] and/or sodium chloride) in the pharmaceutical composition in addition to a botulinum neurotoxin active ingredient. A pharmaceutical composition is therefore a formulation which is suitable for diagnostic, therapeutic or cosmetic administration to a subject, such as a human patient. The pharmaceutical composition can be: in a lyophilized or vacuum dried condition, a solution formed after reconstitution of the lyophilized or vacuum dried pharmaceutical composition with saline or water, for example, or; as a solution that does not require reconstitution. As stated, a pharmaceutical composition can be liquid or solid. A pharmaceutical composition can be animal-protein free.

"Repellant electromagnetic field" means a charge, field, or current that repels the injected material, for example a magnetic or electric field or charge.

"Substantially free" means present at a level of less than one percent by weight of a culture medium, fermentation medium, pharmaceutical composition or other material in which the weight percent of a substance is assessed.

"Therapeutic formulation" means a formulation that can be used to treat and thereby alleviate a disorder or a disease and/or symptom associated thereof, such as a disorder or a disease characterized by an activity of a peripheral muscle.

"Therapeutically effective amount" means the level, amount or concentration of an agent (e.g. such as a botulinum toxin or pharmaceutical composition comprising botulinum toxin) needed to treat a disease, disorder or condition without causing significant negative or adverse side effects.

"Toxin-naive" means a patient who has not been administered a neurotoxin, for example a clostridial toxin, for example BoNT/A.

"Treat," "treating," or "treatment" means an alleviation or a reduction (which includes some reduction, a significant reduction a near total reduction, and a total reduction), resolution or prevention (temporarily or permanently) of an disease, disorder or condition, so as to achieve a desired therapeutic or cosmetic result, such as by healing of injured or damaged tissue, or by altering, changing, enhancing, improving, ameliorating and/or beautifying an existing or perceived disease, disorder or condition.

"Unit" or "U" means an amount of active BoNT standardized to have equivalent neuromuscular blocking effect as a Unit of commercially available BoNT/A.

Methods of Treatment

In embodiments, methods of localizing the injected materials can comprise applying an energy field, for example an electric charge, field or current, or combinations thereof, to at least one injection site, or applying an energy field, for example an energy field, for example an electric charge, field or current, or combinations thereof, surrounding at least one injection site, and combinations thereof. For example, an energy field, for example an attractive electric charge, field or current, or combinations thereof, can be applied directly on top of the injection site. In embodiments, an energy field, for example a repellant electric charge, field or current, or combinations thereof, can be applied around the perimeter of one or multiple injection sites. These methods can be combined such that attractive and repellant forces are applied.

In embodiments, methods of minimizing an immune response caused by injected materials can comprise applying an energy field, for example an electric charge, field or current, or combinations thereof, to at least one injection site, or surrounding at least one injection site. For example, an attractive energy field, for example an electric charge, field or current, or combinations thereof, can be applied directly on top of the injection site. In embodiments, a repellant energy field, for example an electric charge, field or current, or combinations thereof, can be applied around the perimeter or a part thereof of one or multiple injection sites. These methods can be combined such that attractive and repellant fields are applied.

In embodiments the energy field can comprise, for example, an electric field, electric charge, electric current, a magnetic field, a combination thereof, or the like. For example, an electric field can be applied to an injection site through the use of an electrode supplying a suitable voltage to produce an attractive field to "attract" the materials. In embodiments, an electric field can be applied to surround (either partially or completely) an injection site through the use of an electrode supplying a suitable voltage to produce a repellant field to "repel" the materials. In embodiments, both attractive and repellant field are applied. In this manner, the spread or dissipation of the injected materials can be reduced or eliminated.

In embodiments, an electric field can comprise voltages suitable for application to the mammal. For example, a suitable electric field can comprise voltages appropriate to application to the body of a mammal, for example a human.

In various embodiments the difference of the standard potentials of the electrodes providing attractant and repellant fields can be in a range from about 0.05 V to approximately about 10.0 V. For example, the standard potential can be about 0.05 V, about 0.06 V, about 0.07 V, about 0.08 V, about 0.09 V, about 0.1 V, about 0.2 V, about 0.3 V, about 0.4 V, about 0.5 V, about 0.6 V, about 0.7 V, about 0.8 V, about 0.9 V, about 1.0 V, about 1.1 V, about 1.2 V, about 1.3 V, about 1.4 V, about 1.5 V, about 1.6 V, about 1.7 V, about 1.8 V, about 1.9 V, about 2.0 V, about 2.1 V, about 2.2 V, about 2.3 V, about 2.4 V, about 2.5 V, about 2.6 V, about 2.7 V, about 2.8 V, about 2.9 V, about 3.0 V, about 3.1 V, about 3.2 V, about 3.3 V, about 3.4 V, about 3.5 V, about 3.6 V, about 3.7 V, about 3.8 V, about 3.9 V, about 4.0 V, about 4.1 V, about 4.2 V, about 4.3 V, about 4.4 V, about 4.5 V, about 4.6 V, about 4.7 V, about 4.8 V, about 4.9 V, about 5.0 V, about 5.1 V, about 5.2 V, about 5.3 V, about 5.4 V, about 5.5 V, about 5.6 V, about 5.7 V, about 5.8 V, about 5.9 V, about 6.0 V, about 6.1 V, about 6.2 V, about 6.3 V, about 6.4 V, about 6.5 V, about 6.6 V, about 6.7 V, about 6.8 V, about 6.9 V, about 7.0 V, about 7.1 V, about 7.2 V, about 7.3 V, about 7.4 V, about 7.5 V, about 7.6 V, about 7.7 V, about 7.8 V, about 7.9 V, about 8.0 V, about 8.1 V, about 8.2 V, about 8.3 V, about 8.4 V, about 8.5 V, about 8.6 V, about 8.7 V, about 8.8 V, about 8.9 V, about 9.0 V, about 10.0 V, or the like.

In embodiments, the electric field between the attractant and repellant electrodes can be, for example, 20 volt/cm, 19 volt/cm, 18 volt/cm, 17 volt/cm, 16 volt/cm, 15 volt/cm, 14 volt/cm, 13 volt/cm, 12 volt/cm, 11 volt/cm, 10 volt/cm, 9 volt/cm, 8 volt/cm, 7 volt/cm, 6 volt/cm, 5 volt/cm, 4 volt/cm, 3 volt/cm, 2 volt/cm, 1 volt/cm, or the like.

In embodiments, the electric field between the attractant and repellant electrodes can be, for example, between 20 volt/cm and 1 v/cm, between 19 volt/cm and 2 v/cm, between 18 volt/cm and 3 v/cm, between 17 volt/cm and 4 v/cm, between 16 volt/cm and 5 v/cm, between 15 volt/cm and 6 v/cm, between 14 volt/cm and 7 v/cm, between 13 volt/cm and 8 v/cm, between 12 volt/cm and 9 v/cm, between 11 volt/cm and 10 v/cm, or the like. In embodiments, the electric field between the attractant and repellant electrodes can be, for example, no more than 20 volt/cm, no more than 19 volt/cm, no more than 18 volt/cm, no more than 17 volt/cm, no more than 16 volt/cm, no more than 15 volt/cm, no more than 14 volt/cm, no more than 13 volt/cm, no more than 12 volt/cm, no more than 11 volt/cm, no more than 10 volt/cm, no more than 9 volt/cm, no more than 8 volt/cm, no more than 7 volt/cm, no more than 6 volt/cm, no more than 5 volt/cm, no more than 4 volt/cm, no more than 3 volt/cm, no more than 2 volt/cm, no more than 1 volt/cm, or the like.

In embodiments, the electric field between the attractant and repellant electrodes can be, for example, no less than 20 volt/cm, no less than 19 volt/cm, no less than 18 volt/cm, no less than 17 volt/cm, no less than 16 volt/cm, no less than 15 volt/cm, no less than 14 volt/cm, no less than 13 volt/cm, no less than 12 volt/cm, no less than 11 volt/cm, no less than 10 volt/cm, no less than 9 volt/cm, no less than 8 volt/cm, no less than 7 volt/cm, no less than 6 volt/cm, no less than 5 volt/cm, no less than 4 volt/cm, no less than 3 volt/cm, no less than 2 volt/cm, no less than 1 volt/cm, or the like.

Embodiments can comprise an electric current between the attractant and repellant electrodes. In embodiments, systems and devices disclosed herein can produce a low level electric current between the attractant and repellant electrodes of between for example about 1 and about 200 micro-amperes, between about 10 and about 190 micro-amperes, between about 20 and about 180 micro-amperes, between about 30 and about 170 micro-amperes, between about 40 and about 160 micro amperes, between about 50 and about 150 micro-amperes, between about 60 and about 140 micro-amperes, between about 70 and about 130 microamperes, between about 80 and about 120 micro-amperes, between about 90 and about 100 micro-amperes, between about 100 and about 150 micro-amperes, between about 150 and about 200 micro-amperes, between about 200 and about 250 micro-amperes, between about 250 and about 300 micro-amperes, between about 300 and about 350 micro-amperes, between about 350 and about 400 micro-amperes, between about 400 and about 450 micro-amperes, between about 450 and about 500 micro-amperes, between about 500 and about 550 micro-amperes, between about 550 and about 600 micro-amperes, between about 600 and about 650 micro-amperes, between about 650 and about 700 micro-amperes, between about 700 and about 750 micro-amperes, between about 750 and about 800 micro-amperes, between about 800 and about 850 micro-amperes, between about 850 and about 900 micro-amperes, between about 900 and about 950 micro-amperes, between about 950 and about 1000 micro-amperes (1 milli-amp [mA]), between about 1.0 and about 1.1 mA, between about 1.1 and about 1.2 mA, between about 1.2 and about 1.3 mA, between about 1.3 and about 1.4 mA, between about 1.4 and about 1.5 mA, between about 1.5 and about 1.6 mA, between about 1.6 and about 1.7 mA, between about 1.7 and about 1.8 mA, between about 1.8 and about 1.9 mA, between about 1.9 and about 2.0 mA, between about 2.0 and about 2.1 mA, between about 2.1 and about 2.2 mA, between about 2.2 and about 2.3 mA, between about 2.3 and about 2.4 mA, between about 2.4 and about 2.5 mA, between about 2.5 and about 2.6 mA, between about 2.6 and about 2.7 mA, between about 2.7 and about 2.8 mA, between about 2.8 and about 2.9 mA, between about 2.9 and about 3.0 mA, between about 3.0 and about 3.1 mA, between about 3.1 and about 3.2 mA, between about 3.2 and about 3.3 mA, between about 3.3 and about 3.4 mA, between about 3.4 and about 3.5 mA, between about 3.5 and about 3.6 mA, between about 3.6 and about 3.7 mA, between about 3.7 and about 3.8 mA, between about 3.8 and about 3.9 mA, between about 3.9 and about 4.0 mA, between about 4.0 and about 4.1 mA, between about 4.1 and about 4.2 mA, between about 4.2 and about 4.3 mA, between about 4.3 and about 4.4 mA, between about 4.4 and about 4.5 mA, between about 4.5 and about 5.0 mA, between about 5.0 and about 5.5 mA, between about 5.5 and about 6.0 mA, between about 6.0 and about 6.5 mA, between about 6.5 and about 7.0 mA, between about 7.5 and about 8.0 mA, between about 8.0 and about 8.5 mA, between about 8.5 and about 9.0 mA, between about 9.0 and about 9.5 mA, between about 9.5 and about 10.0 mA, between about 10.0 and about 10.5 mA, between about 10.5 and about 11.0 mA, between about 11.0 and about 11.5 mA, between about 11.5 and about 12.0 mA, between about 12.0 and about 12.5 mA, between about 12.5 and about 13.0 mA, between about 13.0 and about 13.5 mA, between about 13.5 and about 14.0 mA, between about 14.0 and about 14.5 mA, between about 14.5 and about 15.0 mA, or the like.

In embodiments, systems and devices disclosed herein can produce a low level electric current of between for example about 1 micro-ampere and about 1 milli-ampere, between about 50 and about 800 micro-amperes, between about 200 and about 600 microamperes, between about 400 and about 500 micro-amperes, or the like.

In embodiments, systems and devices disclosed herein can produce a low level electric current of about 10 micro-amperes, about 20 micro-amperes, about 30 microamperes, about 40 micro-amperes, about 50 micro-amperes, about 60 micro-amperes, about 70 micro-amperes, about 80 micro-amperes, about 90 micro-amperes, about 100 micro-amperes, about 110 micro-amperes, about 120 micro-amperes, about 130 microamperes, about 140 micro-amperes, about 150 micro-amperes, about 160 micro-amperes, about 170 micro-amperes, about 180 micro-amperes, about 190 micro-amperes, about 200 micro-amperes, about 210 micro-amperes, about 220 micro-amperes, about 240 microamperes, about 260 micro-amperes, about 280 micro-amperes, about 300 micro-amperes, about 320 micro-amperes, about 340 micro-amperes, about 360 micro-amperes, about 380 micro-amperes, about 400 micro-amperes, about 450 micro-amperes, about 500 microamperes, about 550 micro-amperes, about 600 micro-amperes, about 650 micro-amperes, about 700 micro-amperes, about 750 micro-amperes, about 800 micro-amperes, about 850 micro-amperes, about 900 micro-amperes, about 950 micro-amperes, about 1 milli-ampere (mA), about 1.1 mA, about 1.2 mA, about 1.3 mA, about 1.4 mA, about 1.5 mA, about 1.6 mA, about 1.7 mA, about 1.8 mA, about 1.9 mA, about 2.0 mA, about 2.1 mA, about 2.2 mA, about 2.3 mA, about 2.4 mA, about 2.5 mA, about 2.6 mA, about 2.7 mA, about 2.8 mA, about 2.9 mA, about 3.0 mA, about 3.1 mA, about 3.2 mA, about 3.3 mA, about 3.4 mA, about 3.5 mA, about 3.6 mA, about 3.7 mA, about 3.8 mA, about 3.9 mA, about 4.0 mA, about 4.1 mA, about 4.2 mA, about 4.3 mA, about 4.4 mA, about 4.5 mA, about 4.6 mA, about 4.7 mA, about 4.8 mA, about 4.9 mA, about 5.0 mA, about 5.1 mA, about 5.2 mA, about 5.3 mA, about 5.4 mA, about 5.5 mA, about 5.6 mA, about 5.7 mA, about 5.8 mA, about 5.9 mA, about 6.0 mA, about 6.1 mA, about 4.2 mA, about 6.3 mA, about 6.4 mA, about 6.5 mA, about 6.6 mA, about 6.7 mA, about 6.8 mA, about 6.9 mA, about 7.0 mA, about 7.1 mA, about 7.2 mA, about 7.3 mA, about 7.4 mA, about 7.5 mA, about 7.6 mA, about 7.7 mA, about 7.8 mA, about 7.9 mA, about 8.0 mA, about 8.1 mA, about 8.2 mA, about 8.3 mA, about 8.4 mA, about 8.5 mA, about 8.6 mA, about 8.7 mA, about 8.8 mA, about 8.9 mA, about 9.0 mA, about 9.1 mA, about 9.2 mA, about 9.3 mA, about 9.4 mA, about 9.5 mA, about 9.6 mA, about 9.7 mA, about 9.8 mA, about 9.9 mA, about 10.0 mA, about 10.1 mA, about 10.2 mA, about 10.3 mA, about 10.4 mA, about 10.5 mA, about 10.6 mA, about 10.7 mA, about 10.8 mA, about 10.9 mA, about 11.0 mA, about 11.1 mA, about 11.2 mA, about 11.3 mA, about 11.4 mA, about 11.5 mA, about 11.6 mA, about 11.7 mA, about 11.8 mA, about 11.9 mA, about 12.0 mA, about 12.1 mA, about 12.2 mA, about 12.3 mA, about 12.4 mA, about 12.5 mA, about 12.6 mA, about 12.7 mA, about 12.8 mA, about 12.9 mA, about 13.0 mA, about 13.1 mA, about 13.2 mA, about 13.3 mA, about 13.4 mA, about 13.5 mA, about 13.6 mA, about 13.7 mA, about 13.8 mA, about 13.9 mA, about 14.0 mA, about 14.1 mA, about 14.2 mA, about 14.3 mA, about 14.4 mA, about 14.5 mA, about 14.6 mA, about 14.7 mA, about 14.8 mA, about 14.9 mA, about 15.0 mA, about 15.1 mA, about 15.2 mA, about 15.3 mA, about 15.4 mA, about 15.5 mA, about 15.6 mA, about 15.7 mA, about 15.8 mA, or the like.

In embodiments, the disclosed systems and devices can produce a low level electric current of not more than 10 micro-amperes, or not more than about 20 micro-amperes, not more than about 30 micro-amperes, not more than about 40 micro-amperes, not more than about 50 micro-amperes, not more than about 60 micro-amperes, not more than about 70 micro-amperes, not more than about 80 micro-amperes, not more than about 90 micro-amperes, not more than about 100 micro-amperes, not more than about 110 micro-amperes, not more than about 120 micro-amperes, not more than about 130 micro-amperes, not more than about 140 micro-amperes, not more than about 150 micro-amperes, not more than about 160 micro-amperes, not more than about 170 micro-amperes, not more than about 180 micro-amperes, not more than about 190 micro-amperes, not more than about 200 micro-amperes, not more than about 210 micro-amperes, not more than about 220 micro-amperes, not more than about 230 micro-amperes, not more than about 240 micro-amperes, not more than about 250 micro-amperes, not more than about 260 micro-amperes, not more than about 270 micro-amperes, not more than about 280 micro-amperes, not more than about 290 micro-amperes, not more than about 300 micro-amperes, not more than about 310 micro-amperes, not more than about 320 micro-amperes, not more than about 340 micro-amperes, not more than about 360 micro-amperes, not more than about 380 micro-amperes, not more than about 400 micro-amperes, not more than about 420 micro-amperes, not more than about 440 micro-amperes, not more than about 460 micro-amperes, not more than about 480 micro-amperes, not more than about 500 micro-amperes, not more than about 520 micro-amperes, not more than about 540 micro-amperes, not more than about 560 micro-amperes, not more than about 580 micro-amperes, not more than about 600 micro-amperes, not more than about 620 micro-amperes, not more than about 640 micro-amperes, not more than about 660 micro-amperes, not more than about 680 micro-amperes, not more than about 700 micro-amperes, not more than about 720 micro-amperes, not more than about 740 micro-amperes, not more than about 760 micro-amperes, not more than about 780 micro-amperes, not more than about 800 micro-amperes, not more than about 820 micro-amperes, not more than about 840 micro-amperes, not more than about 860 micro-amperes, not more than about 880 micro-amperes, not more than about 900 micro-amperes, not more than about 920 micro-amperes, not more than about 940 micro-amperes, not more than about 960 micro-amperes, not more than about 980 micro-amperes, not more than about 1 milli-ampere (mA), not more than about 1.1 mA, not more than about 1.2 mA, not more than about 1.3 mA, not more than about 1.4 mA, not more than about 1.5 mA, not more than about 1.6 mA, not more than about 1.7 mA, not more than about 1.8 mA, not more than about 1.9 mA, not more than about 2.0 mA, not more than about 2.1 mA, not more than about 2.2 mA, not more than about 2.3 mA, not more than about 2.4 mA, not more than about 2.5 mA, not more than about 2.6 mA, not more than about 2.7 mA, not more than about 2.8 mA, not more than about 2.9 mA, not more than about 3.0 mA, not more than about 3.1 mA, not more than about 3.2 mA, not more than about 3.3 mA, not more than about 3.4 mA, not more than about 3.5 mA, not more than about 3.6 mA, not more than about 3.7 mA, not more than about 3.8 mA, not more than about 3.9 mA, not more than about 4.0 mA, not more than about 4.1 mA, not more than about 4.2 mA, not more than about 4.3 mA, not more than about 4.4 mA, not more than about 4.5 mA, not more than about 4.6 mA, not more than about 4.7 mA, not more than about 4.8 mA, not more than about 4.9 mA, not more than about 5.0 mA, not more than about 5.1 mA, not more than about 5.2 mA, not more than about 5.3 mA, not more than about 5.4 mA, not more than about 5.5 mA, not more than about 5.6 mA, not more than about 5.7 mA, not more than about 5.8 mA, not more than about 5.9 mA, not more than about 6.0 mA, not more than about 6.1 mA, not more than about 4.2 mA, not more than about 6.3 mA, not more than about 6.4 mA, not more than about 6.5 mA, not more than about 6.6 mA, not more than about 6.7 mA, not more than about 6.8 mA, not more than about 6.9 mA, not more than about 7.0 mA, not more than about 7.1 mA, not more than about 7.2 mA, not more than about 7.3 mA, not more than about 7.4 mA, not more than about 7.5 mA, not more than about 7.6 mA, not more than about 7.7 mA, not more than about 7.8 mA, not more than about 7.9 mA, not more than about 8.0 mA, not more than about 8.1 mA, not more than about 8.2 mA, not more than about 8.3 mA, not more than about 8.4 mA, not more than about 8.5 mA, not more than about 8.6 mA, not more than about 8.7 mA, not more than about 8.8 mA, not more than about 8.9 mA, not more than about 9.0 mA, not more than about 9.1 mA, not more than about 9.2 mA, not more than about 9.3 mA, not more than about 9.4 mA, not more than about 9.5 mA, not more than about 9.6 mA, not more than about 9.7 mA, not more than about 9.8 mA, not more than about 9.9 mA, not more than about 10.0 mA, not more than about 10.1 mA, not more than about 10.2 mA, not more than about 10.3 mA, not more than about 10.4 mA, not more than about 10.5 mA, not more than about 10.6 mA, not more than about 10.7 mA, not more than about 10.8 mA, not more than about 10.9 mA, not more than about 1.0 mA, not more than about 11.1 mA, not more than about 1.2 mA, not more than about 11.3 mA, not more than about 11.4 mA, not more than about 11.5 mA, not more than about 11.6 mA, not more than about 11.7 mA, not more than about 11.8 mA, not more than about 11.9 mA, not more than about 12.0 mA, not more than about 12.1 mA, not more than about 12.2 mA, not more than about 12.3 mA, not more than about 12.4 mA, not more than about 12.5 mA, not more than about 12.6 mA, not more than about 2.7 mA, not more than about 12.8 mA, not more than about 12.9 mA, not more than about 13.0 mA, not more than about 13.1 mA, not more than about 13.2 mA, not more than about 13.3 mA, not more than about 13.4 mA, not more than about 13.5 mA, not more than about 13.6 mA, not more than about 13.7 mA, not more than about 13.8 mA, not more than about 13.9 mA, not more than about 14.0 mA, not more than about 14.1 mA, not more than about 14.2 mA, not more than about 14.3 mA, not more than about 14.4 mA, not more than about 14.5 mA, not more than about 14.6 mA, not more than about 14.7 mA, not more than about 14.8 mA, not more than about 14.9 mA, not more than about 15.0 mA, not more than about 15.1 mA, not more than about 15.2 mA, not more than about 15.3 mA, not more than about 15.4 mA, not more than about 15.5 mA, not more than about 15.6 mA, not more than about 15.7 mA, not more than about 15.8 mA, and the like.

In embodiments, systems and devices disclosed herein can produce a low level electric current of not less than about 11.8 mA, not less than about 11.9 mA, not less than about 12.0 mA, not less than about 12.1 mA, not less than about 12.2 mA, not less than about 12.3 mA, not less than about 12.4 mA, not less than about 12.5 mA, not less than about 12.6 mA, not less than about 12.7 mA, not less than about 12.8 mA, not less than about 12.9 mA, not less than about 13.0 mA, not less than about 13.1 mA, not less than about 13.2 mA, not less than about 13.3 mA, not less than about 13.4 mA, not less than about 13.5 mA, not less than about 13.6 mA, not less than about 13.7 mA, not less than about 13.8 mA, not less than about 13.9 mA, not less than about 14.0 mA, not less than about 14.1 mA, not less than about 14.2 mA, not less than about 14.3 mA, not less than about 14.4 mA, not less than about 14.5 mA, not less than about 14.6 mA, not less than about 14.7 mA, not less than about 14.8 mA, not less than about 14.9 mA, not less than about 15.0 mA, not less than about 15.1 mA, not less than about 15.2 mA, not less than about 15.3 mA, not less than about 15.4 mA, not less than about 15.5 mA, not less than about 15.6 mA, not less than about 15.7 mA, not less than about 15.8 mA, and the like.

In embodiments, disclosed devices can provide an electric field of greater than physiological strength to a depth (as measured from the surface of the device) of, at least 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or more.

In embodiments, disclosed devices can provide an electric field of greater than physiological strength to a depth (as measured from the surface of the device) of, not more than 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or more.

In active embodiments, for example utilizing a TENS device, TENS is applied at high frequency (>50 Hz) with an intensity below motor contraction (sensory intensity) or low frequency (<10 Hz) with an intensity that produces motor contraction. Disclosed embodiments typically utilize an intensity below that required to cause motor contraction. In embodiments, the attractant electrode is placed atop the treatment area.

In embodiments, an electric charge, field, current, or combinations thereof is applied using a system comprising devices comprising electrodes. For example, a disclosed device can comprise conductive electrodes. In embodiments, the device comprises attractive and repellant electrodes, said attractive and repellant electrodes comprising opposing charges. For example, in powered devices, electrodes can comprise platinum, with one of the attractive/repellant electrodes comprising a positive charge, and the other comprising negative charge.

Disclosed embodiments can be used to limit the amount of non-therapeutic materials to be injected into a patient. For example, in embodiments, the vessel containing the material to be injected is subjected to an electromagnetic field that attracts the therapeutic material, and the injection material is withdrawn from the vessel in the vicinity of the attractant electromagnetic field.

Injected Materials

In embodiments, the injected materials can comprise pharmaceutical compositions. For example, suitable pharmaceutical compositions can comprise any materials typically administered via injection (to include needle-less injection). Such compositions can comprise neurotoxins, for example botulinum toxins.

For example, in disclosed embodiments, the neurotoxin is formulated in unit dosage form; for example, it can be provided as a sterile solution in a vial or as a vial or sachet containing a lyophilized powder for reconstituting in a suitable vehicle such as saline for injection. Although examples of routes of administration and dosages are provided, the appropriate route of administration and dosage are generally determined on a case by case basis by the attending physician. Such determinations are routine to one of ordinary skill in the art. For example, the route and dosage for administration of a Clostridial neurotoxin according to the present disclosure can be selected based upon criteria such as the solubility characteristics of the neurotoxin chosen as well as the intensity and scope of the condition being treated.

The neurotoxin can be administered in an amount of between about $10^{-3}$ U/kg and about 35 U/kg. In an embodiment, the neurotoxin is administered in an amount of between about $10^{-2}$ U/kg and about 25 U/kg. In another embodiment, the neurotoxin is administered in an amount of between about $10^{-1}$ U/kg and about 15 U/kg. In another embodiment, the neurotoxin is administered in an amount of between about 1 U/kg and about 10 U/kg. In many instances, an administration of from about 1 unit to about 500 units of a neurotoxin, such as a botulinum type E, provides effective therapeutic relief. In an embodiment, from about 5 units to about 200 units of a neurotoxin, such as a botulinum type E, can be used and in another embodiment, from about 10 units to about 100 units of a neurotoxin, such as a botulinum type E, can be locally administered into a target tissue such as a muscle.

In embodiments, administration can comprise a dose of about 10 units of a neurotoxin, or about 20 units of a neurotoxin, or about 30 units of a neurotoxin, or about 40 units of a neurotoxin, or about 50 units of a neurotoxin, or about 60 units of a neurotoxin, or about 70 units of a neurotoxin, or about 80 units of a neurotoxin, or about 90 units of a neurotoxin, or about 100 units of a neurotoxin, or about 110 units of a neurotoxin, or about 120 units of a neurotoxin, or about 130 units of a neurotoxin, or about 140 units of a neurotoxin, or about 150 units of a neurotoxin, or about 160 units of a neurotoxin, or about 170 units of a neurotoxin, or about 180 units of a neurotoxin, or about 190 units of a neurotoxin, or about 200 units of a neurotoxin, or about 210 units of a neurotoxin, or about 220 units of a neurotoxin, or about 230 units of a neurotoxin, or about 240 units of a neurotoxin, or about 250 units of a neurotoxin, or about 260 units of a neurotoxin, or about 270 units of a neurotoxin, or about 280 units of a neurotoxin, or about 290 units of a neurotoxin, or about 290 units of a neurotoxin, or about 300 units of a neurotoxin, or about 310 units of a neurotoxin, or about 320 units of a neurotoxin, or about 330 units of a neurotoxin, or about 340 units of a neurotoxin, or about 350 units of a neurotoxin, or about 360 units of a neurotoxin, or about 370 units of a neurotoxin, or about 380 units of a neurotoxin, or about 390 units of a neurotoxin, or about 400 units of a neurotoxin, or about 410 units of a neurotoxin, or about 420 units of a neurotoxin, or about 430 units of a neurotoxin, or about 440 units of a neurotoxin, or about 450 units of a neurotoxin, or about 460 units of a neurotoxin, or about 470 units of a neurotoxin, or about 480 units of a neurotoxin, or about 490 units of a neurotoxin, or about 500 units of a neurotoxin, or the like.

In embodiments, administration can comprise a dose of not less than 10 units of a neurotoxin, not less than 20 units of a neurotoxin, not less than 30 units of a neurotoxin, not less than 40 units of a neurotoxin, not less than 50 units of a neurotoxin, not less than 60 units of a neurotoxin, not less than 70 units of a neurotoxin, not less than 80 units of a neurotoxin, not less than 90 units of a neurotoxin, not less than 100 units of a neurotoxin, not less than 110 units of a neurotoxin, not less than 120 units of a neurotoxin, not less than 130 units of a neurotoxin, not less than 140 units of a neurotoxin, not less than 150 units of a neurotoxin, not less than 160 units of a neurotoxin, or about 170 units of a neurotoxin, or about 180 units of a neurotoxin, not less than 190 units of a neurotoxin, not less than 200 units of a neurotoxin, not less than 210 units of a neurotoxin, not less than 220 units of a neurotoxin, not less than 230 units of a neurotoxin, not less than 240 units of a neurotoxin, not less than 250 units of a neurotoxin, not less than 260 units of a neurotoxin, not less than 270 units of a neurotoxin, not less than 280 units of a neurotoxin, not less than 290 units of a neurotoxin, or about 290 units of a neurotoxin, not less than 300 units of a neurotoxin, not less than 310 units of a neurotoxin, not less than 320 units of a neurotoxin, not less than 330 units of a neurotoxin, not less than 340 units of a neurotoxin, not less than 350 units of a neurotoxin, not less than 360 units of a neurotoxin, not less than 370 units of a neurotoxin, not less than 380 units of a neurotoxin, not less than 390 units of a neurotoxin, not less than 400 units of a neurotoxin, not less than 410 units of a neurotoxin, not less than 420 units of a neurotoxin, not less than 430 units of a neurotoxin, not less than 440 units of a neurotoxin, not less than 450 units of a neurotoxin, not less than 460 units of a neurotoxin, not less than 470 units of a neurotoxin, not less than 480 units of a neurotoxin, not less than 490 units of a neurotoxin, not less than 500 units of a neurotoxin, or the like.

In embodiments, administration can comprise a dose of not more than 10 units of a neurotoxin, not more than 20 units of a neurotoxin, not more than 30 units of a neurotoxin, not more than 40 units of a neurotoxin, not more than 50 units of a neurotoxin, not more than 60 units of a neurotoxin, not more than 70 units of a neurotoxin, not more than 80 units of a neurotoxin, not more than 90 units of a neurotoxin, not more than 100 units of a neurotoxin, not more than 110 units of a neurotoxin, not more than 120 units of a neurotoxin, not more than 130 units of a neurotoxin, not more than 140 units of a neurotoxin, not more than 150 units of a neurotoxin, not more than 160 units of a neurotoxin, not more 170 units of a neurotoxin, not more than 180 units of a neurotoxin, not more than 190 units of a neurotoxin, not more than 200 units of a neurotoxin, not more than 210 units of a neurotoxin, not more than 220 units of a neurotoxin, not more than 230 units of a neurotoxin, not more than 240 units of a neurotoxin, not more than 250 units of a neurotoxin, not more than 260 units of a neurotoxin, not more than 270 units of a neurotoxin, not more than 280 units of a neurotoxin, not more than 290 units of a neurotoxin, not more than 300 units of a neurotoxin, not more than 310 units of a neurotoxin, not more than 320 units of a neurotoxin, not more than 330 units of a neurotoxin, not more than 340 units of a neurotoxin, not more than 350 units of a neurotoxin, not more than 360 units of a neurotoxin, not more than 370 units of a neurotoxin, not more than 380 units of a neurotoxin, not more than 390 units of a neurotoxin, not more than 400 units of a neurotoxin, not more than 410 units of a neurotoxin, not more than 420 units of a neurotoxin, not more than 430 units of a neurotoxin, not more than 440 units of a neurotoxin, not more than 450 units of a neurotoxin, not more than 460 units of a neurotoxin, not more than 470 units of a neurotoxin, not more than 480 units of a neurotoxin, not more than 490 units of a neurotoxin, not more than 500 units of a neurotoxin, or the like.

In embodiments, the dose of the neurotoxin is expressed in protein amount or concentration. For example, in embodiments the neurotoxin can be administered in an amount of between about 0.2 ng and 20 ng. In an embodiment, the neurotoxin is administered in an amount of between about 0.3 ng and 19 ng, about 0.4 ng and 18 ng, about 0.5 ng and 17 ng, about 0.6 ng and 16 ng, about 0.7 ng and 15 ng, about 0.8 ng and 14 ng, about 0.9 ng and 13 ng, about 1.0 ng and 12 ng, about 1.5 ng and 11 ng, about 2 ng and 10 ng, about 5 ng and 7 ng, and the like, into a target tissue such as a muscle.

In embodiments, neurotoxin administration can comprise a total dose of between 5 and 7 ng, between 7 and 9 ng, between 9 and 11 ng, between 11 and 13 ng, between 13 and 15 ng, between 15 and 17 ng, between 17 and 19 ng, or the like.

In embodiments, administration can comprise a total dose of not more than 5 ng, not more than 6 ng, not more than 7 ng, not more than 8 ng, not more than 9 ng, not more than 10 ng, not more than 11 ng, not more than 12 ng, not more than 13 ng, not more than 14 ng, not more than 15 ng, not more than 16 ng, not more than 17 ng, not more than 18 ng, not more than 19 ng, not more than 20 ng, or the like.

In embodiments, neurotoxin administration can comprise a total dose of not less than 5 ng, not less than 6 ng, not less than 7 ng, not less than 8 ng, not less than 9 ng, not less than 10 ng, not less than 11 ng, not less than 12 ng, not less than 13 ng, not less than 14 ng, not less than 15 ng, not less than 16 ng, not less than 17 ng, not less than 18 ng, not less than 19 ng, not less than 20 ng, or the like.

In embodiments, administration can comprise a total dose of about 0.1 ng of a neurotoxin, 0.2 ng of a neurotoxin, 0.3 ng of a neurotoxin, 0.4 ng of a neurotoxin, 0.5 ng of a neurotoxin, 0.6 n of a neurotoxin, 0.7 ng of a neurotoxin, 0.8 ng of a neurotoxin, 0.9 ng of a neurotoxin, 1.0 ng of a neurotoxin, 1.1 ng of a neurotoxin, 1.2 ng of a neurotoxin, 1.3 ng of a neurotoxin, 1.4 ng of a neurotoxin, 1.5 ng of a neurotoxin, 1.6 ng of a neurotoxin, 1.7 ng of a neurotoxin, 1.8 ng of a neurotoxin, 1.9 ng of a neurotoxin, 2.0 ng of a neurotoxin, 2.1 ng of a neurotoxin, 2.2 ng of a neurotoxin, 2.3 ng of a neurotoxin, 2.4 ng of a neurotoxin, 2.5 ng of a neurotoxin, 2.6 ng of a neurotoxin, 2.7 ng of a neurotoxin, 2.8 ng of a neurotoxin, 2.9 ng of a neurotoxin, 3.0 ng of a neurotoxin, 3.1 ng of a neurotoxin, 3.2 ng of a neurotoxin, 3.3 ng of a neurotoxin, 3.4 ng of a neurotoxin, 3.5 ng of a neurotoxin, 3.6 n of a neurotoxin, 3.7 n of a neurotoxin, 3.8 n of a neurotoxin, 3.9 ng of a neurotoxin, 4.0 ng of a neurotoxin, 4.1 ng of a neurotoxin, 4.2 ng of a neurotoxin, 4.3 ng of a neurotoxin, 4.4 ng of a neurotoxin, 4.5 ng of a neurotoxin, 5 ng of a neurotoxin, 6 ng of a neurotoxin, 7 ng of a neurotoxin, 8 ng of a neurotoxin, 9 ng of a neurotoxin, 10 ng of a neurotoxin, 11 ng of a neurotoxin, 12 ng of a neurotoxin, 13 ng of a neurotoxin, 14 ng of a neurotoxin, 15 ng of a neurotoxin, 16 ng of a neurotoxin, 17 ng of a neurotoxin, 18 ng of a neurotoxin, 19 ng of a neurotoxin, 20 ng of a neurotoxin, or the like.

In embodiments, administration can comprise a dose per administration of about 0.1 ng of a neurotoxin, 0.2 ng of a neurotoxin, 0.3 ng of a neurotoxin, 0.4 ng of a neurotoxin, 0.5 ng of a neurotoxin, 0.6 n of a neurotoxin, 0.7 ng of a neurotoxin, 0.8 ng of a neurotoxin, 0.9 ng of a neurotoxin, 1.0 ng of a neurotoxin, 1.1 ng of a neurotoxin, 1.2 ng of a neurotoxin, 1.3 ng of a neurotoxin, 1.4 ng of a neurotoxin, 1.5 ng of a neurotoxin, 1.6 ng of a neurotoxin, 1.7 ng of a neurotoxin, 1.8 ng of a neurotoxin, 1.9 ng of a neurotoxin, 2.0 ng of a neurotoxin, 2.1 ng of a neurotoxin, 2.2 ng of a neurotoxin, 2.3 ng of a neurotoxin, 2.4 ng of a neurotoxin, 2.5 ng of a neurotoxin, 2.6 ng of a neurotoxin, 2.7 ng of a neurotoxin, 2.8 ng of a neurotoxin, 2.9 ng of a neurotoxin, 3.0 ng of a neurotoxin, 3.1 ng of a neurotoxin, 3.2 ng of a neurotoxin, 3.3 ng of a neurotoxin, 3.4 ng of a neurotoxin, 3.5 ng of a neurotoxin, 3.6 n of a neurotoxin, 3.7 n of a neurotoxin, 3.8 n of a neurotoxin, 3.9 ng of a neurotoxin, 4.0 ng of a neurotoxin, 4.1 ng of a neurotoxin, 4.2 ng of a neurotoxin, 4.3 ng of a neurotoxin, 4.4 ng of a neurotoxin, 4.5 ng of a neurotoxin, 5 ng of a neurotoxin, 6 ng of a neurotoxin, 7 ng of a neurotoxin, 8 ng of a neurotoxin, 9 ng of a neurotoxin, 10 ng of a neurotoxin, or the like.

Ultimately, however, both the quantity of toxin administered and the frequency of its administration will be at the discretion of the physician responsible for the treatment and will be commensurate with questions of safety and the effects produced by the toxin.

Embodiments comprise injection of a volume of dermal filler, for example hyaluronic acid.

In embodiments, the volume of hyaluronic acid composition comprises, for example, 0.3 ml, 0.4 ml, 0.5 ml, 0.6 ml, 0.7 ml, 0.8 ml, 0.9 ml, 1 ml, 1.5 ml, 2 ml, 2.5 ml, 3 ml, 3.5 ml, 4 ml, 4.5 ml, 5 ml, 5.5 ml, 6 ml, 6.5 ml, 7 ml, 7.5 ml, 8 ml, 8.5 ml, 9 ml, 9.5 ml, 10 ml, 12 ml, 14 ml, 16 ml, 18 ml, 20 ml, 22 ml, 24 ml, 26 ml, 27 ml, 28 ml, 29 ml, 30 ml, or the like.

In embodiments, the volume of dermal filler composition comprises, for example, not more than 0.3 ml, not more than 0.4 ml, not more than 0.5 ml, not more than 0.6 ml, not more than 0.7 ml, not more than 0.8 ml, not more than 0.9 ml, not more than 1 ml, not more than 1.5 ml, not more than 2 ml, not more than 2.5 ml, not more than 3 ml, not more than 3.5 ml, not more than 4 ml, not more than 4.5 ml, not more than 5 ml, not more than 5.5 ml, not more than 6 ml, not more than 6.5 ml, not more than 7 ml, not more than 7.5 ml, not more than 8 ml, not more than 8.5 ml, not more than 9 ml, not more than 9.5 ml, not more than 10 ml, not more than 12 ml, not more than 14 ml, not more than 16 ml, not more than 18 ml, not more than 20 ml, not more than 22 ml, not more than 24 ml, not more than 26 ml, not more than 27 ml, not more than 28 ml, not more than 29 ml, not more than 30 ml, or the like.

In embodiments, the volume of dermal filler composition comprises, for example, not less than 0.3 ml, not less than 0.4 ml, not less than 0.5 ml, not less than 0.6 ml, not less than 0.7 ml, not more than 0.8 ml, not more than 0.9 ml, not less than 1 ml, not less than 1.5 ml, not less than 2 ml, not less than 2.5 ml, not less than 3 ml, not less than 3.5 ml, not less than 4 ml, not less than 4.5 ml, not less than 5 ml, not less than 5.5 ml, not less than 6 ml, not less than 6.5 ml, not less than 7 ml, not less than 7.5 ml, not more than 8 ml, not less than 8.5 ml, not less than 9 ml, not less than 9.5 ml, not more than 10 ml, not less than 12 ml, not less than 14 ml, not less than 16 ml, not less than 18 ml, not less than 20 ml, not less than 22 ml, not less than 24 ml, not less than 26 ml, not less than 27 ml, not less than 28 ml, not less than 29 ml, not less than 30 ml, or the like.

In embodiments, the treatment device or devices applying the electric charge, field, or current is applied surrounding or to the treatment area for, for example, 30 seconds, 45 seconds, 60 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes, 60 minutes, 61 minutes, 62 minutes, 63 minutes, 63 minutes, 64 minutes, 65 minutes, 66 minutes, 67 minutes, 68 minutes, 69 minutes, 70 minutes, 71 minutes, 72 minutes, 73 minutes, 74 minutes, 75 minutes, 76 minutes, 77 minutes, 78 minutes, 79 minutes, 80 minutes, 81 minutes, 82 minutes, 83 minutes, 84 minutes, 85 minutes, 86 minutes, 87 minutes, 88 minutes, 89 minutes, 90 minutes, 91 minutes, 92 minutes, 93 minutes, 94 minutes, 95 minutes, 96 minutes, 97 minutes, 98 minutes, 99 minutes, 100 minutes, 101 minutes, 102 minutes, 103 minutes, 104 minutes, 105 minutes, 106 minutes, 107 minutes, 108 minutes, 109 minutes, 110 minutes, 111 minutes, 112 minutes, 113 minutes, 114 minutes, 115 minutes, 116 minutes, 117 minutes, 118 minutes, 119 minutes, 120 minutes, or more, or the like.

In embodiments, the treatment device or devices applying the electric charge, field, or current is applied surrounding or to the treatment area for, for example, not less than 30 seconds, not less than 45 seconds, not less than not less than 60 seconds, not less than 1 minute, not less than 2 minutes, not less than 3 minutes, not less than 4 minutes, not less than 5 minutes, not less than 6 minutes, not less than 7 minutes, not less than 8 minutes, not less than 9 minutes, not less than 10 minutes, not less than 11 minutes, not less than 12 minutes, not less than 13 minutes, not less than 14 minutes, not less than 15 minutes, not less than 16 minutes, not less than 17 minutes, not less than 18 minutes, not less than 19 minutes, not less than 20 minutes, not less than 21 minutes, not less than 22 minutes, not less than 23 minutes, not less than 24 minutes, not less than 25 minutes, 26 minutes, not less than 27 minutes, not less than 28 minutes, not less than 29 minutes, not less than 30 minutes, not less than 31 minutes, not less than 32 minutes, not less than 33 minutes, not less than 34 minutes, not less than 35 minutes, not less than 36 minutes, not less than not less than 37 minutes, not less than 38 minutes, not less than 39 minutes, not less than 40 minutes, not less than 41 minutes, not less than 42 minutes, not less than 43 minutes, not less than 44 minutes, not less than 45 minutes, not less than 46 minutes, not less than 47 minutes, not less than 48 minutes, not less than 49 minutes, not less than 50 minutes, not less than 51 minutes, not less than 52 minutes, not less than 53 minutes, not less than 54 minutes, not less than 55 minutes, not less than 56 minutes, not less than 57 minutes, not less than 58 minutes, not less than 59 minutes, not less than 60 minutes, not less than 61 minutes, not less than 62 minutes, not less than 63 minutes, not less than 64 minutes, not less than 65 minutes, not less than 66 minutes, not less than 67 minutes, not less than 68 minutes, not less than 69 minutes, not less than 70 minutes, not less than 71 minutes, not less than 72 minutes, not less than 73 minutes, not less than 74 minutes, not less than 75 minutes, not less than 76 minutes, not less than 77 minutes, not less than 78 minutes, not less than 79 minutes, not less than 80 minutes, not less than 81 minutes, not less than 82 minutes, not less than 83 minutes, not less than 84 minutes, not less than 85 minutes, not less than 86 minutes, not less than 87 minutes, not less than 88 minutes, not less than 89 minutes, not less than 90 minutes, not less than 91 minutes, not less than 92 minutes, not less than 93 minutes, not less than 94 minutes, not less than 95 minutes, not less than 96 minutes, not less than 97 minutes, not less than 98 minutes, not less than 99 minutes, not less than 100 minutes, not less than 101 minutes, not less than 102 minutes, not less than 103 minutes, not less than 104 minutes, not less than 105 minutes, 106 minutes, 1 not less than 07 minutes, not less than 108 minutes, not less than 109 minutes, not less than 110 minutes, not less than 111 minutes, not less than 112 minutes, not less than 113 minutes, not less than 114 minutes, not less than 115 minutes, not less than 116 minutes, not less than 117 minutes, not less than 118 minutes, not less than 119 minutes, not less than 120 minutes, or more, or the like.

In embodiments, the treatment device or devices applying the electric charge, field, or current is applied surrounding or to the treatment area for, for example, not more than 30 seconds, not more than 45 seconds, not more than not more than 60 seconds, not more than 1 minute, not more than 2 minutes, not more than 3 minutes, not more than 4 minutes, not more than 5 minutes, not more than 6 minutes, not more than 7 minutes, not more than 8 minutes, not more than 9 minutes, not more than 10 minutes, not more than 11 minutes, not more than 12 minutes, not more than 13 minutes, not more than 14 minutes, not more than 15 minutes, not more than 16 minutes, not more than 17 minutes, not more than 18 minutes, not more than 19 minutes, not more than 20 minutes, not more than 21 minutes, not more than 22 minutes, not more than 23 minutes, not more than 24 minutes, not more than 25 minutes, not more than 26 minutes, not more than 27 minutes, not more than 28 minutes, not more than 29 minutes, not more than 30 minutes, not more than 31 minutes, not more than 32 minutes, not more than 33 minutes, not more than 34 minutes, not more than 35 minutes, not more than 36 minutes, not more than 37 minutes, not more than 38 minutes, not more than 39 minutes, not more than 40 minutes, not more than 41 minutes, not more than 42 minutes, not more than 43 minutes, not more than 44 minutes, not more than 45 minutes, not more than 46 minutes, not more than 47 minutes, not more than 48 minutes, not more than 49 minutes, not more than 50 minutes, not more than 51 minutes, not more than 52 minutes, not more than 53 minutes, not more than 54 minutes, not more than 55 minutes, not more than 56 minutes, not more than 57 minutes, not more than 58 minutes, not more than 59 minutes, not more than 60 minutes, not more than 61 minutes, not more than 62 minutes, not more than 63 minutes, not more than 64 minutes, not more than 65 minutes, not more than 66 minutes, not more than 67 minutes, not more than 68 minutes, not more than 69 minutes, not more than 70 minutes, not more than 71 minutes, not more than 72 minutes, not more than 73 minutes, not more than 74 minutes, not more than 75 minutes, not more than 76 minutes, not more than 77 minutes, not more than 78 minutes, not more than 79 minutes, not more than 80 minutes, not more than 81 minutes, not more than 82 minutes, not more than 83 minutes, not more than 84 minutes, not more than 85 minutes, not more than 86 minutes, not more than 87 minutes, not more than 88 minutes, not more than 89 minutes, not more than 90 minutes, not more than 91 minutes, not more than 92 minutes, not more than 93 minutes, not more than 94 minutes, not more than 95 minutes, not more than 96 minutes, not more than 97 minutes, not more than 98 minutes, not more than 99 minutes, not more than 100 minutes, not more than 101 minutes, not more than 102 minutes, not more than 103 minutes, not more than 104 minutes, not more than 105 minutes, not more than 106 minutes, not more than 107 minutes, not more than 108 minutes, not more than 109 minutes, not more than 110 minutes, not more than 111 minutes, not more than 112 minutes, not more than 113 minutes, not more than 114 minutes, not more than 115 minutes, not more than 116 minutes, not more than 117 minutes, not more than 118 minutes, not more than 119 minutes, not more than 120 minutes, or more, or the like.

In embodiments, the attractive/repellant electric charge, fired, or current are applied to and about the treatment site. For example, in embodiments, electrodes are powered by, for example between 1 and 10 V and applied about 1 cm apart, with the attractive electrode applied upon the treatment site and the repellent electrode applied to form a partial or complete perimeter around the treatment site. The distance between the attractive and repellant electrodes can be determined based on the voltage applied to affect the most beneficial treatment. For example, the attractive and repellant electrodes can be applied 1 mm apart, 2 mm apart, 3 mm apart, 4 mm apart, 5 mm apart, 6 mm apart, 7 mm apart, 8 mm apart, 9 mm apart, 10 mm apart, 11 mm apart, 12 mm apart, 13 mm apart, 14 mm apart, 15 mm apart, 16 mm apart, 17 mm apart, 18 mm apart, 19 mm apart, 2 cm apart, 2.5 cm apart, 3 cm apart, 3.5 cm apart, 4 cm apart, 4.5 cm apart, 5 cm apart, 5.5 cm apart, 6 cm apart, 6.5 cm apart, 7 cm apart, 7.5 cm apart, 8 cm apart, 8.5 cm apart, 9 cm apart, 10 cm apart, 10.5 cm apart, 11 cm apart, 11.5 cm apart, 12 cm apart, 12.5 cm apart, 13 cm apart, 13.5 cm apart, 14 cm apart, 14.5 cm apart, 15 cm apart, 15.5 cm apart, 16 cm apart, 16.5 cm apart, 17 cm apart, or more, or the like.

In embodiments, the distance between the attractive and repellant electrodes can be, for example, at least 1 mm apart, at least 2 mm apart, at least 3 mm apart, at least 4 mm apart, at least 5 mm apart, at least 6 mm apart, at least 7 mm apart, at least 8 mm apart, at least 9 mm apart, at least 10 mm apart, at least 11 mm apart, at least 12 mm apart, at least 13 mm apart, at least 14 mm apart, at least 15 mm apart, at least 16 mm apart, at least 17 mm apart, at least 18 mm apart, at least 19 mm apart, at least 2 cm apart, at least 2.5 cm apart, at least 3 cm apart, at least 3.5 cm apart, at least 4 cm apart, at least 4.5 cm apart, at least 5 cm apart, at least 5.5 cm apart, at least 6 cm apart, at least 6.5 cm apart, at least 7 cm apart, at least 7.5 cm apart, at least 8 cm apart, at least 8.5 cm apart, at least 9 cm apart, at least 10 cm apart, at least 10.5 cm apart, at least 11 cm apart, at least 11.5 cm apart, at least 12 cm apart, at least 12.5 cm apart, at least 13 cm apart, at least 13.5 cm apart, at least 14 cm apart, at least 14.5 cm apart, at least 15 cm apart, at least 15.5 cm apart, at least 16 cm apart, at least 16.5 cm apart, at least 17 cm apart, or more, or the like.

In embodiments, the distance between the attractive and repellant electrodes can be, for example, not more than 1 mm apart, not more than 2 mm apart, not more than 3 mm apart, not more than 4 mm apart, not more than 5 mm apart, not more than 6 mm apart, not more than 7 mm apart, not more than 8 mm apart, not more than 9 mm apart, not more than 10 mm apart, not more than 11 mm apart, not more than 12 mm apart, not more than 13 mm apart, not more than 14 mm apart, not more than 15 mm apart, not more than 16 mm apart, not more than 17 mm apart, not more than 18 mm apart, not more than 19 mm apart, not more than 2 cm apart, not more than 2.5 cm apart, not more than 3 cm apart, not more than 3.5 cm apart, not more than 4 cm apart, not more than 4.5 cm apart, not more than 5 cm apart, not more than 5.5 cm apart, not more than 6 cm apart, not more than 6.5 cm apart, not more than 7 cm apart, at not more than 7.5 cm apart, not more than 8 cm apart, not more than 8.5 cm apart, not more than 9 cm apart, not more than 10 cm apart, not more than 10.5 cm apart, not more than 11 cm apart, not more than 11.5 cm apart, not more than 12 cm apart, not more than 12.5 cm apart, not more than 13 cm apart, not more than 13.5 cm apart, not more than 14 cm apart, not more than 14.5 cm apart, not more than 15 cm apart, not more than 15.5 cm apart, not more than 16 cm apart, not more than 16.5 cm apart, not more than 17 cm apart, or more, or the like.

In embodiments, the distance between the attractive and repellant electrodes can be, for example, between 1 and 20 mm, 2 and 18 mm, 4 and 16 mm, 6 and 14 mm, 8 and 12 mm, or the like. In embodiments, the distance between the attractive and repellant electrodes can be, for example, between 1 and 10 mm, 1 and 9 mm, 1 and 8 mm, 1 and 7 mm, 1 and 6 mm, 1 and 5 mm, 1 and 4 mm, 1 and 3 mm, 1 and 2 mm, or the like. In embodiments, the distance between the attractive and repellant electrodes can be, for example, between 2 and 10 mm, 2 and 9 mm, 2 and 8 mm, 2 and 7 mm, 2 and 6 mm 2 and 5 mm, 2 and 4 mm, 2 and 3 mm, or the like.

In embodiments, the distance between the attractive and repellant electrodes can be, for example, between at least 1 and 20 mm, at least 2 and 18 mm, at least 4 and 16 mm, at least 6 and 14 mm, at least 8 and 12 mm, or the like. In embodiments, the distance between the attractive and repellant electrodes can be, for example, between at least 1 and 10 mm, at least 1 and 9 mm, at least 1 and 8 mm, at least 1 and 7 mm, at least 1 and 6 mm, at least 1 and 5 mm, at least 1 and 4 mm, at least 1 and 3 mm, at least 1 and 2 mm, or the like. In embodiments, the distance between the attractive and repellant electrodes can be, for example, between at least 2 and 10 mm, at least 2 and 9 mm, at least 2 and 8 mm, at least 2 and 7 mm, at least 2 and 6 mm, at least 2 and 5 mm, at least 2 and 4 mm, at least 2 and 3 mm, or the like.

In embodiments, the distance between the attractive and repellant electrodes can be, for example, between not more than 1 and 20 mm, not more than 2 and 18 mm, not more than 4 and 16 mm, not more than 6 and 14 mm, not more than 8 and 12 mm, or the like. In embodiments, the distance between the attractive and repellant electrodes can be, for example, between not more than 1 and 10 mm, not more than 1 and 9 mm, not more than 1 and 8 mm, not more than 1 and 7 mm, not more than 1 and 6 mm, not more than 1 and 5 mm, not more than 1 and 4 mm, not more than 1 and 3 mm, not more than 1 and 2 mm, or the like. In embodiments, the distance between the attractive and repellant electrodes can be, for example, between not more than 2 and 10 mm, not more than 2 and 9 mm, not more than 2 and 8 mm, not more than 2 and 7 mm, not more than 2 and 6 mm, not more than 2 and 5 mm, not more than 2 and 4 mm, not more than 2 and 3 mm, or the like.

In embodiments, disclosed devices can comprise a circular or "donut" shaped device (including a void in the center) comprising an electrode producing a repellant field, for example an electric field. For example, disclosed devices can comprise an electrode producing a repellant electric field that can be applied with the void directly over the treatment site and the body of the device surrounding the treatment site. This type of embodiment can be particularly suitable for use with treatments where no spread of the injected material is desired. For example, in methods comprising administration of a neurotoxin to the patient's head, for example for treatment of migraine or depression or pain, disclosed devices can be applied prior to the injections, then the injection is made through the void region.

Disclosed compositions suitable for use with disclosed devices can comprise cosmetic pharmaceutical compositions, such as dermal fillers.

EXAMPLES

1) Use of an Electric Field to Minimize Neurotoxin Spread

A 44 year old male patient is going to be treated to minimize glabellar lines with BoNT/A. Prior to administering the toxin via needle injection, the doctor applies a disclosed embodiment that generates a positive electric field in a perimeter within 10 mm surrounding the intended injection sites. Then, the doctor injects 5 sites with 4 U of the BoNT/A to the typical glabellar lines treatment sites. The patient wears the embodiment producing the positive electric field for three hours. The patient experiences no ptosis.

2) Use of an Electric Field to Minimize Neurotoxin Spread

A 49 year old male patient is going to be treated to minimize glabellar lines with BoNT/E. Prior to administering the toxin via needle injection, the doctor applies a disclosed embodiment that generates a positive electric field in a perimeter within 10 mm surrounding the intended injection sites. Then, the doctor injects 5 sites with 4 U of the BoNT/E to the typical glabellar lines treatment sites. The patient wears the embodiment producing the positive electric field for three hours. The patient experiences no ptosis.

3) Use of an Electric Field to Minimize Neurotoxin Spread

A 32 year old female patient is going to be treated to minimize glabellar lines with BoNT/B. Prior to administering the toxin via needle injection, the doctor applies a disclosed embodiment that generates a positive electric field in a perimeter within 10 mm surrounding the intended injection sites. Then, the doctor injects 5 sites with 4 U of the BoNT/B to the typical glabellar lines treatment sites. The patient wears the embodiment producing the positive electric field for three hours. The patient experiences no ptosis.

4) Use of an Electric Field to Minimize Neurotoxin Spread

A 27 year old male patient is going to be treated to minimize glabellar lines with BoNT/A. Prior to administering the toxin via needle injection, the doctor applies a disclosed embodiment comprising a platinum electrode powered by a 5V power source that generates a positive electric field in a perimeter within 10 mm surrounding the intended injection sites. Then, the doctor injects 5 sites with 4 U of the BoNT/A to the typical glabellar lines treatment sites. The patient wears the embodiment producing the positive electric field for three hours. The patient experiences no ptosis.

5) Use of an Electric Field to Minimize Neurotoxin Spread

A 27 year old male patient is going to be treated to minimize glabellar lines with BoNT/A. Prior to administering the toxin via needle injection, the doctor applies a disclosed embodiment comprising a platinum electrode powered by a 3V power source that generates a positive electric field in a perimeter within 10 mm surrounding the intended injection sites. Then, the doctor injects 5 sites with 4 U of the BoNT/A to the typical glabellar lines treatment sites. The patient wears the embodiment producing the positive electric field for three hours. The patient experiences no ptosis.

6) Use of an Electric Field to Minimize Neurotoxin Spread

A 33 year old female patient is going to be treated to minimize crows feet with BoNT/A. Prior to administering the toxin via needle injection, the doctor applies a disclosed embodiment comprising a zinc electrode that generates a positive electric field in a perimeter surrounding the intended injection sites. Then, the doctor injects 5 sites with 4 U of the BoNT/A to the typical crows feet treatment sites. Following the injections, the doctor applies a disclosed embodiment comprising a silver electrode that generates a negative electric field directly on top of the injection sites. The patient wears the embodiments producing the positive and negative electric fields for 30 minutes. The patient experiences no ptosis.

7) Use of an Electric Field to Minimize Neurotoxin Spread

A 54 year old female patient is going to be treated to minimize crows feet with BoNT/A. Prior to administering the toxin via needle injection, the doctor applies a disclosed embodiment comprising a zinc electrode that generates a positive electric field in a perimeter surrounding the intended injection sites. Then, the doctor injects 5 sites with 5 U of the BoNT/E to the typical crows feet treatment sites. Following the injections, the doctor applies a disclosed embodiment comprising a silver electrode that generates a negative electric field directly on top of the injection sites. The patient wears the embodiments producing the positive and negative electric fields for 30 minutes. The patient experiences no ptosis.

8) Use of an Electric Field to Minimize Neurotoxin Spread

A 33 year old female patient is going to be treated to minimize crows feet with BoNT/B. Prior to administering the toxin via needle injection, the doctor applies a disclosed embodiment that generates a positive electric field in a perimeter surrounding the intended injection sites. Then, the doctor injects 5 sites with 4 U of the BoNT/B to the typical crows feet treatment sites. Following the injections, the doctor applies a disclosed embodiment that generates a negative electric field directly on top of the 5 injection sites. The patient wears the embodiments producing the positive and negative electric fields for three 30 minutes. The patient experiences no spread of the toxin from the treatment site.

9) Use of an Electric Field to Minimize Dermal Filler Spread

A 54 year old male patient is going to be treated with hyaluronic acid. Prior to administering the filler via needle injection, the doctor applies a disclosed embodiment that generates a negative electric field in a perimeter surrounding the intended injection sites. The patient wears the embodiment producing the positive electric field for three hours. The patient experiences no diffusion of the filler.

10) Use of an Electric Field to Minimize Dermal Filler Spread

A 43 year old female patient is going to be treated with hyaluronic acid. Prior to administering the filler via needle injection, the doctor applies a disclosed embodiment that generates a negative electric field in a perimeter surrounding the intended injection sites. Following the injections, the doctor applies a disclosed embodiment that generates a positive electric field directly on top of the injection sites. The patient wears the embodiments producing the positive and negative electric fields for 30 minutes. The patient experiences no diffusion of the filler.

11) Use of a Tens to Minimize Dermal Filler Spread

A 33 year old female patient is going to be treated to minimize crows feet with BoNT/A. Prior to administering the toxin via needle injection, the doctor applies a TENS device to minimize spread of the neurotoxin. Prior to injection, positive electrodes of the TENS is applied to repel the toxin from beyond the treatment area, while the negative electrode is placed directly on top of the injection sites. The intensity of the TENS is increased until the patient reports a tingling sensation.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present disclosure, which is defined solely by the claims. Accordingly, embodiments of the present disclosure are not limited to those precisely as shown and described.

Certain embodiments are described herein, including the best mode known to the inventor for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

Groupings of alternative embodiments, elements, or steps of the present disclosure are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the disclosure are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the disclosure and does not pose a limitation on the scope otherwise claimed. No language in the present specification should be construed as indicating any non-claimed element essential to the practice of embodiments disclosed herein.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present disclosure so claimed are inherently or expressly described and enabled herein.

What is claimed is:

1. A method for limiting a dissipation of a neurotoxin from an injection site, the method comprising:
   a) applying at least one electrode producing a repellant electric field to a skin surface around the injection site, wherein said at least one electrode does not penetrate the skin, thereby producing the repellant electric field across the intact skin surface where dissipation is to be limited, wherein said repellant electric field comprises a positive charge if an isoelectric point of the neurotoxin is greater than pH 7.4, and wherein said repellant electric field comprises a negative charge if the isoelectric point of the neurotoxin is less than pH 7.4; and applying at least another electrode producing an attractive electric field to the skin surface at the injection site, wherein said at least another electrode does not penetrate the skin, thereby producing the attractive field across the intact skin surface, wherein said attractive electric field comprises a negative charge if said isoelectric point is greater than pH 7.4, and wherein said attractive electric field comprises a positive charge if said isoelectric point is less than pH 7.4; and
   b) injecting the neurotoxin; wherein the produced attractive and repellant electric fields limit the dissipation of the neurotoxin.

2. The method of claim 1, wherein said neurotoxin comprises a Clostridial toxin.

3. The method of claim 2, wherein said neurotoxin comprises a native botulinum toxin.

4. The method of claim 3, wherein said botulinum toxin comprises native BoNT/A.

5. The method of claim 3, wherein said botulinum toxin comprises native BoNT/E.

6. The method of claim 3, wherein said botulinum toxin comprises native BoNT/B.

7. The method of claim 2, wherein said neurotoxin comprises a recombinant botulinum toxin.

8. The method of claim 7, wherein said botulinum toxin comprises recombinant BoNT/A.

9. The method of claim 7, wherein said botulinum toxin comprises recombinant BoNT/E.

10. The method of claim 7, wherein said botulinum toxin comprises recombinant BoNT/B.

11. The method of claim 1, wherein said repellant field is applied for at least 30 minutes.

12. The method of claim 11, wherein said repellant field is applied for at least 45 minutes.

13. The method of claim 12, wherein said repellant field is applied for at least 60 minutes.

14. The method of claim 1, wherein said attractive field is applied for at least 30 minutes.

15. The method of claim 14, wherein said attractive field is applied for at least 45 minutes.

16. The method of claim 15, wherein said attractive field is applied for at least 60 minutes.

17. The method of claim 1, wherein said attractive and repellant fields are applied for at least 30 minutes.

18. The method of claim 17, wherein said attractive and repellant fields are applied for at least 45 minutes.

19. The method of claim 18, wherein said attractive and repellant fields are applied for at least 60 minutes.

20. The method of claim 17, wherein said neurotoxin comprises BoNT/A.

21. The method of claim 20, wherein said neurotoxin comprises native BoNT/A.

22. The method of claim 20, wherein said neurotoxin comprises recombinant BoNT/A.

23. The method of claim 17, wherein said neurotoxin comprises BoNT/E.

24. The method of claim 23, wherein said neurotoxin comprises native BoNT/E.

25. The method of claim 23, wherein said neurotoxin comprises recombinant BoNT/E.

26. The method of claim 17, wherein said neurotoxin comprises BoNT/B.

27. The method of claim 26, wherein said neurotoxin comprises native BoNT/B.

28. The method of claim 26, wherein said neurotoxin comprises recombinant BoNT/B.

* * * * *